(12) United States Patent
Hijlkema et al.

(10) Patent No.: US 9,821,125 B2
(45) Date of Patent: Nov. 21, 2017

(54) NEBULIZER AND A METHOD OF MANUFACTURING A NEBULIZER

(71) Applicant: KONINKLIJKE PHILIPS N.V., Eindhoven (NL)

(72) Inventors: Markus Hijlkema, Chichester (GB); Michael James Robbert Leppard, Hunston (GB)

(73) Assignee: Koninklijke Philips N.V., Eindhoven (NL)

( * ) Notice: Subject to any disclaimer, the term of this patent is extended or adjusted under 35 U.S.C. 154(b) by 262 days.

(21) Appl. No.: 14/390,415

(22) PCT Filed: Apr. 26, 2013

(86) PCT No.: PCT/IB2013/053322
§ 371 (c)(1),
(2) Date: Oct. 3, 2014

(87) PCT Pub. No.: WO2013/160883
PCT Pub. Date: Oct. 31, 2013

(65) Prior Publication Data
US 2015/0144128 A1  May 28, 2015

Related U.S. Application Data

(60) Provisional application No. 61/638,523, filed on Apr. 26, 2012.

(51) Int. Cl.
*A61M 11/00* (2006.01)
*B05B 17/00* (2006.01)
(Continued)

(52) U.S. Cl.
CPC ......... *A61M 11/003* (2014.02); *A61M 11/005* (2013.01); *A61M 11/02* (2013.01);
(Continued)

(58) Field of Classification Search
CPC ................ A61M 11/003; A61M 15/0021; A61M 11/02; A61M 11/005; A61M 2205/50;
(Continued)

(56) References Cited

U.S. PATENT DOCUMENTS

| 6,405,934 B1 | 6/2002 | Hess et al. |
| 2002/0175220 A1 | 11/2002 | Pence |

(Continued)

FOREIGN PATENT DOCUMENTS

| EP | 1570912 A2 | 9/2005 |
| EP | 1932597 A2 | 6/2008 |
| JP | S481981 U | 11/1973 |

*Primary Examiner* — Steven Douglas (57) ABSTRACT

There is provided a nebulizer (2), comprising a first plate (20) configured to hold a transducer (14); a second plate (22) having an aperture therein, the first plate being positioned on a first side of the second plate such that the transducer is adjacent the aperture; and a third plate (24) configured to hold a mesh plate through which liquid can pass to form droplets, the third plate being positioned on a second side of the second plate opposite the first side such that the mesh plate (16) is adjacent the aperture, with the aperture, transducer and mesh plate forming a cavity for holding liquid to be nebulized. A method for manufacturing such a nebulizer is also provided.

14 Claims, 5 Drawing Sheets

(51) Int. Cl.
   *A61M 15/00*      (2006.01)
   *A61M 11/02*      (2006.01)
(52) U.S. Cl.
   CPC ..... *A61M 15/0021* (2014.02); *B05B 17/0638* (2013.01); *A61M 2205/50* (2013.01); *A61M 2207/10* (2013.01); *Y10T 29/49396* (2015.01)
(58) Field of Classification Search
   CPC ........... A61M 2207/10; B05B 17/0638; Y10T 29/49396
   See application file for complete search history.

(56) References Cited

U.S. PATENT DOCUMENTS

| | | | |
|---|---|---|---|
| 2005/0032941 A1 | 2/2005 | Hart et al. | |
| 2005/0201870 A1 | 9/2005 | Koerner et al. | |
| 2006/0032941 A1* | 2/2006 | Sheng-Chih | B05B 17/0638 239/102.2 |
| 2006/0243820 A1 | 11/2006 | Ng | |
| 2008/0110453 A1* | 5/2008 | Ross | A61M 15/0085 128/200.16 |
| 2009/0223513 A1* | 9/2009 | Papania | A61M 15/0065 128/200.16 |
| 2009/0236437 A1 | 9/2009 | Schuerle et al. | |
| 2009/0308945 A1* | 12/2009 | Loverich | A01M 1/205 239/4 |
| 2010/0044460 A1* | 2/2010 | Sauzade | B05B 17/0646 239/102.2 |
| 2011/0259334 A1 | 10/2011 | Alfieri et al. | |
| 2013/0072755 A1* | 3/2013 | Papania | A61M 11/005 600/109 |

\* cited by examiner

NEBULIZER AND A METHOD OF MANUFACTURING A NEBULIZER

CROSS-REFERENCE TO PRIOR APPLICATIONS

This application is the U.S. National Phase application under 35 U.S.C. §371 of International Application No. PCT/IB2013/053322, filed on Apr. 26, 2013, which claims the benefit of U.S. Provisional Patent Application No. 61/638,523, filed on Apr. 26, 2012. These applications are hereby incorporated by reference herein.

TECHNICAL FIELD OF THE INVENTION

The invention relates to a nebulizer that nebulizes liquid held therein into fine droplets, for example for inhalation by a user, and a method of manufacturing thereof.

BACKGROUND TO THE INVENTION

Nebulizers, or atomizers as they are sometimes called, are devices that generate a fine spray or aerosol from a liquid. A particularly useful application for nebulizers is to provide a fine spray containing a dissolved or a suspended particulate drug for administration to a patient by inhalation.

Since the patient has to administer a certain amount of medication, the treatment time will be mainly determined by the mass flow rate of the aerosol generated by the nebulizer. Particularly for new medications, like biologics, the medication dose can be large, which means that the treatment time can be up to several hours for nebulizers that are currently on the market.

However, so-called flat plate technology or piezo-cavity-mesh based nebulizers have the potential to offer much higher mass flow rates than conventional nebulizers. In these types of nebulizers, a cavity for the liquid drug is created with an ultrasonic transducer forming one wall and the other opposing wall of the cavity comprising an aperture or mesh plate containing an array of nozzles or holes. When the transducer is activated, ultrasonic pressure waves are created in the liquid in the cavity, causing liquid in the cavity to be pushed through the nozzles to form fine droplets.

Figure 1:
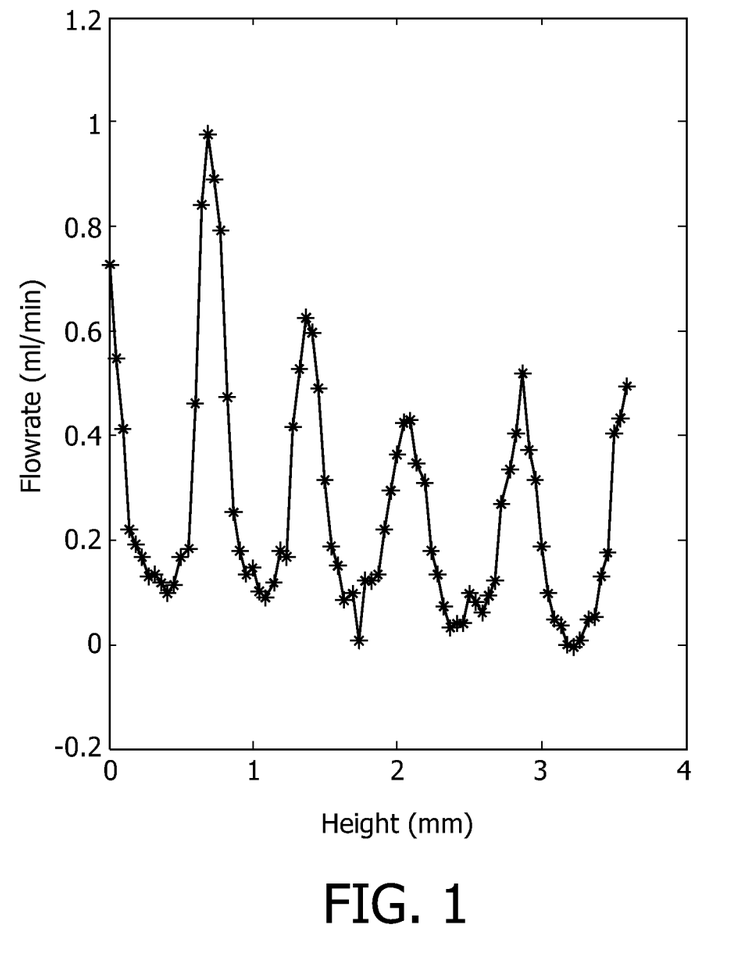

One significant disadvantage with this type of nebulizer, however, is that the mass flow rate achieved by the nebulizer is highly sensitive to the distance between the transducer and the mesh plate. The mass flow rate for a particular flat plate technology nebulizer as a function of the distance between the transducer and mesh plate is shown in FIG. 1. Thus, it can be seen that the mass flow rate halves when the separation (referred to as the 'height' in FIG. 1) between the transducer and mesh plate is 100 microns (0.1 mm) from the optimum separation (around 0.7 mm).

The mass flow rate should be the same for each and every nebulizer produced. Thus, a tolerance requirement is placed on nebulizers such that 90% of nebulizers built should have a mass flow rate within 25% of the target mass flow rate. This requirement can be fulfilled only when the tolerance of the separation distance is such that the standard deviation of this distance is on the order of 10 microns (0.01 mm).

In addition, since the patient is administering medication to his or her lungs, care needs to be taken to keep the nebulizer clean. Residue from the liquids used in the nebulizer can lead to fouling and could become a potential health hazard. Moreover, this residue can subsequently clog the nozzles in the mesh plate, decreasing the output performance of the nebulizer. For current nebulizers, it is recommended that the nebulizer is cleaned by rinsing with hot soapy water of 95° C. on a daily basis. This leads to a requirement for the nebulizer to be able to tolerate around 1800 of these cleaning cycles over its lifetime. Furthermore, the interior of the nebulizer should be easily accessible while at the same time any performance deterioration during the lifetime should be avoided. Therefore, a further desirable feature of the piezo-cavity-mesh type nebulizer is the ability to remove at least the mesh plate from the nebulizer for cleaning or replacement.

These requirements combined demand a nebulizer design that can be manufactured with very small tolerances, high stability, and of course, low cost. These demands are hard to meet with conventional manufacturing technologies like injection-molding.

Therefore, there is a need for an alternative nebulizer and method of manufacturing thereof that meet these requirements.

SUMMARY OF THE INVENTION

Therefore, according to a first aspect of the invention, there is provided a nebulizer, comprising a first plate configured to hold a transducer; a second plate having an aperture therein, the first plate being positioned on a first side of the second plate such that the transducer is adjacent the aperture; and a third plate configured to hold a mesh plate through which liquid can pass to form droplets, the third plate being positioned on a second side of the second plate opposite the first side such that the mesh plate is adjacent the aperture, with the aperture, transducer and mesh plate forming a cavity for holding liquid to be nebulized. By assembling the nebulizer from a number of plates to form the cavity, the nebulizer can be manufactured with very small tolerances, high stability and low cost.

In some embodiments, the thickness of the second plate generally defines the separation between the transducer and the mesh plate. Thus, by controlling the thickness of the second plate during manufacture, the separation between the transducer and mesh plate can be set to the desired amount to ensure efficient operation of the nebulizer.

In preferred embodiments, the nebulizer further comprises a foil layer disposed between the first plate and the second plate to prevent contact between the transducer and liquid to be held in the cavity. Preferably the foil layer is a metal foil since metallic foils absorb little of the mechanical energy provided by the transducer.

In these embodiments, the combined thickness of the foil layer and the thickness of the second plate generally define the separation between the transducer and the mesh plate. Thus, by controlling the thickness of the second plate and foil layer during manufacture, the separation between the transducer and mesh plate can be set to the desired amount to ensure efficient operation of the nebulizer.

Preferably, at least the second plate is metal. Metal is a preferred material for the second plate as it is relatively easy to manufacture the plates to the tolerances required in a nebulizer. Even more preferably, at least the second plate is formed from rolled sheet metal. In preferred embodiments, at least the second plate is stainless steel, since this metal is cheap, thermally stable and won't be corroded or worn through contact with liquid in the cavity.

Preferably the third plate and mesh plate are removably attached to the second plate. This allows the third plate and mesh plate to be removed for cleaning or replacement, and also allows access to the cavity for cleaning.

In some embodiments, the nebulizer further comprises a reservoir chamber for holding further liquid to be nebulized, the reservoir chamber being linked to the cavity via a feed channel in the second plate that is in fluid communication with the first aperture in the second plate and a hole in the first plate.

Preferably at least a part of a lower edge of the hole in the first plate has a jagged or saw-tooth profile, since this helps to encourage liquid to flow from the reservoir chamber through the hole and into the cavity.

In some embodiments, the second plate further comprises a venting channel for venting the cavity.

Preferably, the first plate and second plate are fixedly attached together, for example using glue, adhesive or any other type of bonding material or layer. In preferred embodiments, the first plate and second plate are fixedly attached together using an adhesive or bonding layer, the adhesive or bonding layer comprising spacer particles therein for setting the thickness of the adhesive or bonding layer to a predetermined amount. In these embodiments, the thickness of the second plate and thickness of the adhesive or bonding layer (as determined by the spacer particles) generally defines the separation between the transducer and the mesh plate.

Where the nebulizer comprises a foil layer between the first plate and second plate, the foil layer can be attached to each of the first and second plates using a respective adhesive or bonding layer that comprises spacer particles. In these embodiments, the thickness of the second plate, foil layer and each of the adhesive or bonding layers (as determined by the spacer particles) generally defines the separation between the transducer and the mesh plate.

According to a second aspect of the invention, there is provided a method of manufacturing a nebulizer, the method comprising obtaining a second plate having an aperture therein; attaching a first plate that is configured to hold a transducer to a first side of the second plate such that the transducer is adjacent the aperture; and attaching a third plate that is configured to hold a mesh plate through which liquid can pass to form droplets to a second side of the second plate opposite the first side such that the mesh plate is adjacent the aperture, with the aperture, transducer and mesh plate forming a cavity for holding liquid to be nebulized.

In some embodiments, the step of obtaining a second plate comprises obtaining a second plate having a predetermined thickness, with the thickness of the second plate generally defining the separation between the transducer and the mesh plate. This enables the separation between the transducer and mesh plate to be set to the desired amount to ensure efficient operation of the nebulizer.

In preferred embodiments, the step of attaching the first plate to a first side of the second plate comprises disposing a foil layer between the first plate and the second plate to prevent contact between the transducer and liquid to be held in the cavity. Preferably the foil layer is a metal foil since metallic foils absorb little of the mechanical energy provided by the transducer.

In these embodiments, the combined thickness of the foil layer and the thickness of the second plate generally define the separation between the transducer and the mesh plate. This enables the separation between the transducer and mesh plate to be set to the desired amount to ensure efficient operation of the nebulizer.

Preferably, at least the second plate is metal. Metal is a preferred material for the second plate as it is relatively easy to manufacture the plates to the tolerances required in a nebulizer. Even more preferably, at least the second plate is formed from rolled sheet metal. In preferred embodiments, at least the second plate is stainless steel, since this metal is cheap, thermally stable and won't be corroded or worn through contact with liquid in the cavity.

Preferably the step of attaching the third plate to the second side of the second plate comprises removably attaching the third plate to the second plate. This allows the third plate and mesh plate to be removed for cleaning or replacement, and also allows access to the cavity for cleaning.

In some embodiments, the method further comprises the steps of: forming a hole through the first plate, forming a feed channel in the second plate, and attaching a reservoir chamber for holding further liquid to be nebulized to the first plate, such that the reservoir chamber is linked to the cavity via the feed channel in the second plate and the hole in the first plate.

Preferably the step of forming a hole through the first plate comprises forming a hole such that at least a part of a lower edge of the hole has a jagged or saw-tooth profile, since this helps to encourage liquid to flow from the reservoir chamber through the hole and into the cavity.

In some embodiments, the method further comprises forming a venting channel for venting the cavity in the second plate.

Preferably, the step of attaching the first plate to the second plate comprises fixedly attaching the first and second plates together, for example using glue, adhesive or any other type of bonding material or layer. In preferred embodiments, the step of attaching the first plate and second plate comprises using an adhesive or bonding layer, with the adhesive or bonding layer comprising spacer particles therein for setting the thickness of the adhesive or bonding layer to a predetermined amount. In these embodiments, the thickness of the second plate and thickness of the adhesive or bonding layer (as determined by the spacer particles) generally defines the separation between the transducer and the mesh plate.

Where the step of attaching the first plate to the second plate comprises disposing a foil layer between the first plate and second plate, the step of attaching can comprise using an adhesive or bonding layer that comprises spacer particles to attach the foil layer to each of the first and second plates. In these embodiments, the thickness of the second plate, foil layer and each of the adhesive or bonding layers (as determined by the spacer particles) generally defines the separation between the transducer and the mesh plate.

BRIEF DESCRIPTION OF THE DRAWINGS

For a better understanding of the invention, and to show more clearly how it may be carried into effect, reference will now be made, by way of example only, to the accompanying drawings, in which:

FIG. 1 is a graph illustrating the variation in mass flow rate of a nebulizer with changes in the distance between the transducer and mesh plate;

FIG. 2 is a block diagram of a piezo-cavity-mesh type nebulizer according to the invention;

FIG. 3 is an exploded view of a nebulizer according to an embodiment of the invention;

FIG. 4 shows two perspective views of a nebulizer according to another embodiment of the invention; and FIG. 5 is a flow chart illustrating a method of manufacturing a nebulizer according to an embodiment of the invention.

DETAILED DESCRIPTION OF THE PREFERRED EMBODIMENTS

Figure 2:
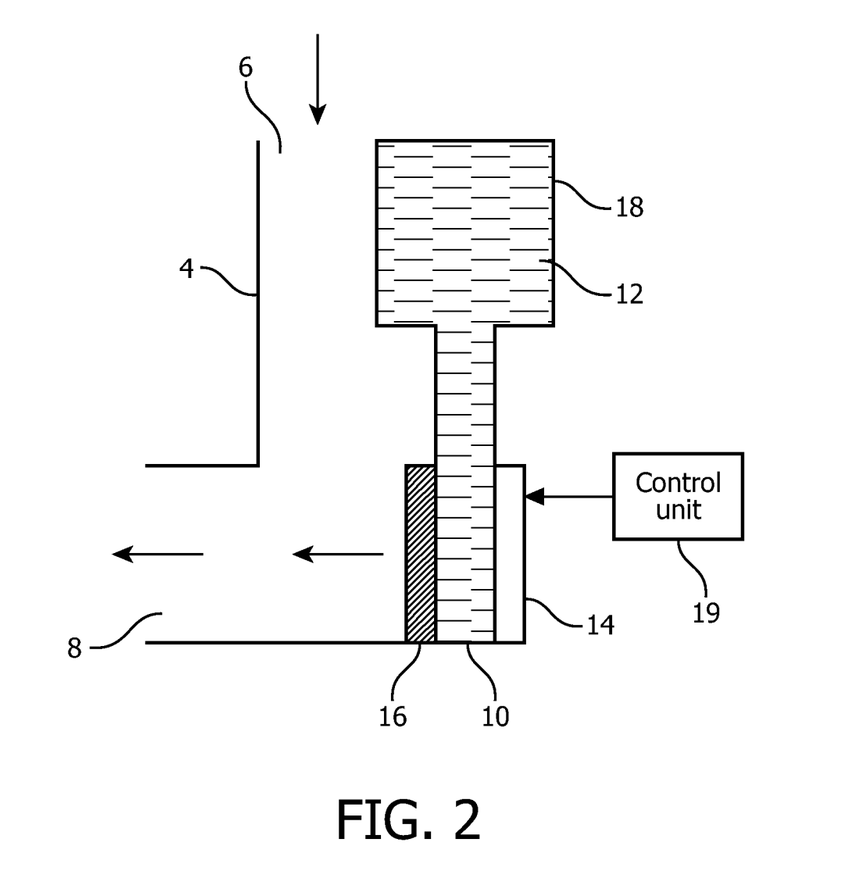

FIG. 2 is a block diagram illustrating a general piezo-cavity-mesh type nebulizer 2 according to the invention. The nebulizer 2 comprises a body 4 having an inlet 6 and an outlet 8 arranged so that when a user of the nebulizer 2 inhales through the outlet 8, air is drawn into and through the nebulizer 2 via the inlet 6 and outlet 8 and into the user's lungs. The outlet 8 is typically provided in the form of a mouthpiece or a facial or nasal mask or in a form that is suitable for connection to a separate replaceable mouthpiece or facial or nasal mask.

The nebulizer 2 comprises a cavity 10 located adjacent to the conduit between the inlet 6 and outlet 8 for holding a liquid 12, for example a medication or drug, to be nebulized (i.e. to be turned into a fine mist or spray). The nebulizer 2 is configured such that fine droplets of the nebulized liquid 12 combine with the air drawn through the nebulizer 2 when the user inhales to deliver a dose of the medication or drug to the user.

One wall of the cavity 10 is formed by an actuator or transducer 14 and the opposite wall of the cavity 10 facing the conduit between the inlet 6 and outlet 8 is formed by a mesh plate 16. The mesh plate 16 is arranged so that liquid droplets passing therethrough enter the air drawn in through the air inlet 6.

The transducer 14 is provided for agitating or vibrating the liquid 12 held in the cavity 10. Preferably, the transducer 14 generates ultrasonic pressure waves in the liquid 12 held in the cavity 10. In the embodiments of the invention that are described further below, the actuator 14 is provided in the form of a piezoelectric element. However, those skilled in the art of nebulizers will appreciate that other forms of actuator 14 can be used in nebulizers according to the invention.

The mesh plate 16 is provided as a wall of the cavity 10 for nebulizing the liquid 12 when the liquid 12 is vibrated by the transducer 14. The mesh plate 16 is typically in the form of a mesh or membrane having a plurality of small holes or nozzles through which small amounts of the liquid can pass. The size (diameter) of the nozzles in the mesh plate 16 determines, among other things, the size of the droplets of liquid produced when the nebulizer 2 is activated, and thus the mass flow rate of the nebulizer 2. The mesh plate 16 is removable from the nebulizer 2 so that it can be cleaned or completely replaced, as required. The mesh plate 16 is preferably formed from platinum, although those skilled in the art will be aware of other suitable materials that can be used. Those skilled in the art will also appreciate that mesh plates 16 are also known as aperture plates or nozzle plates.

In use, the liquid 12 fills the cavity 10 between the transducer 14 and mesh plate 16. It will be appreciated that the liquid 12 in the cavity 10 will be depleted as the nebulizer 2 is operated, and more liquid 12 must be added to the cavity 10 to maintain the liquid 12 at the required height for the nebulizer 2 to continue operating. Therefore, the nebulizer 2 may comprise, or be coupled to, a reservoir chamber 18 that stores liquid for replenishing the liquid 12 in the cavity 10. The liquid from the reservoir chamber 18 may flow into the cavity 10 due to the action of gravity and/or capillary filling.

The nebulizer 2 further comprises a control unit 19 that controls the operation of the nebulizer 2, and in particular outputs signals to the transducer 14 that cause the transducer 14 to vibrate at the required frequency and nebulize the liquid 12.

Figure 3:
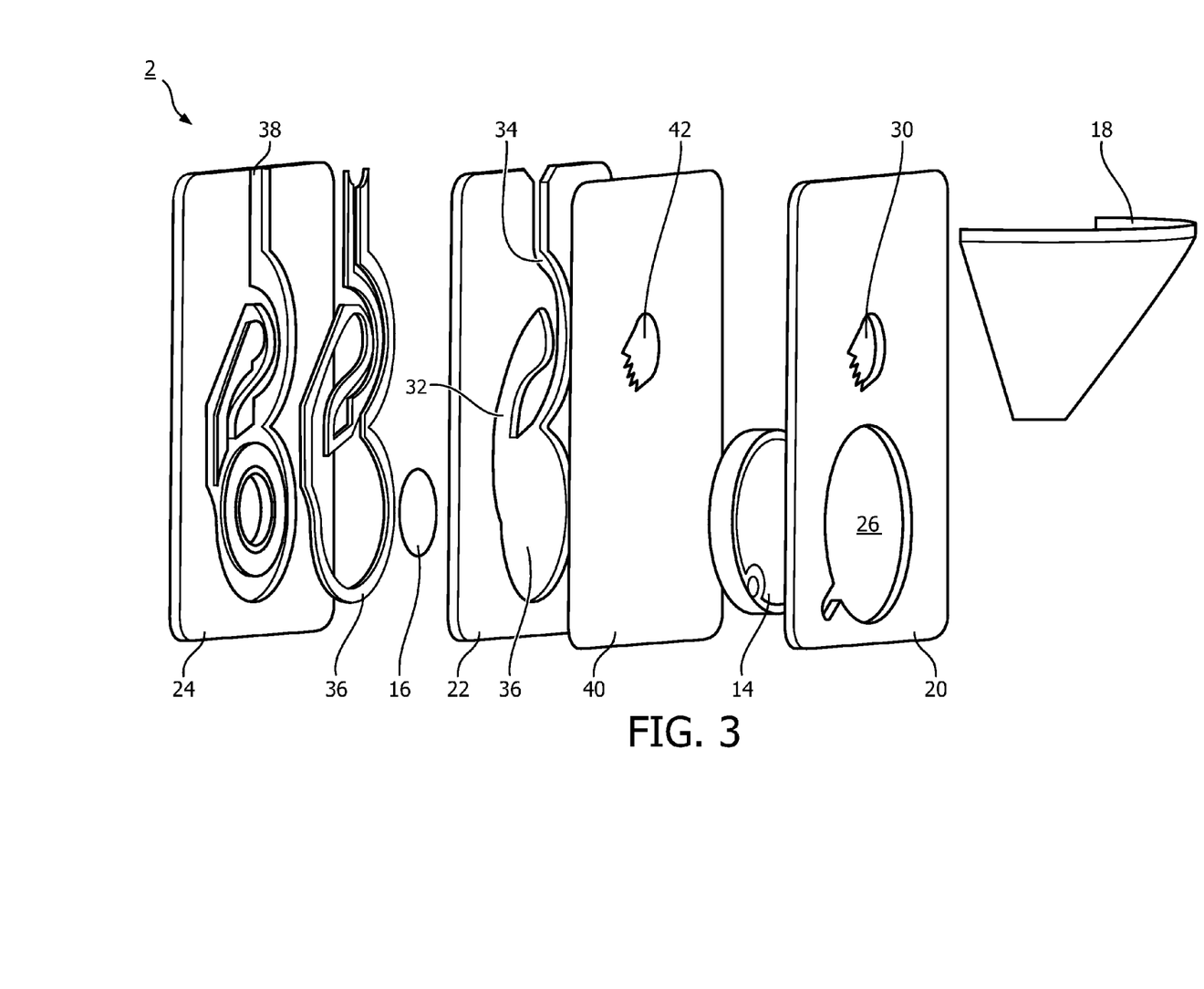
Figure 4:
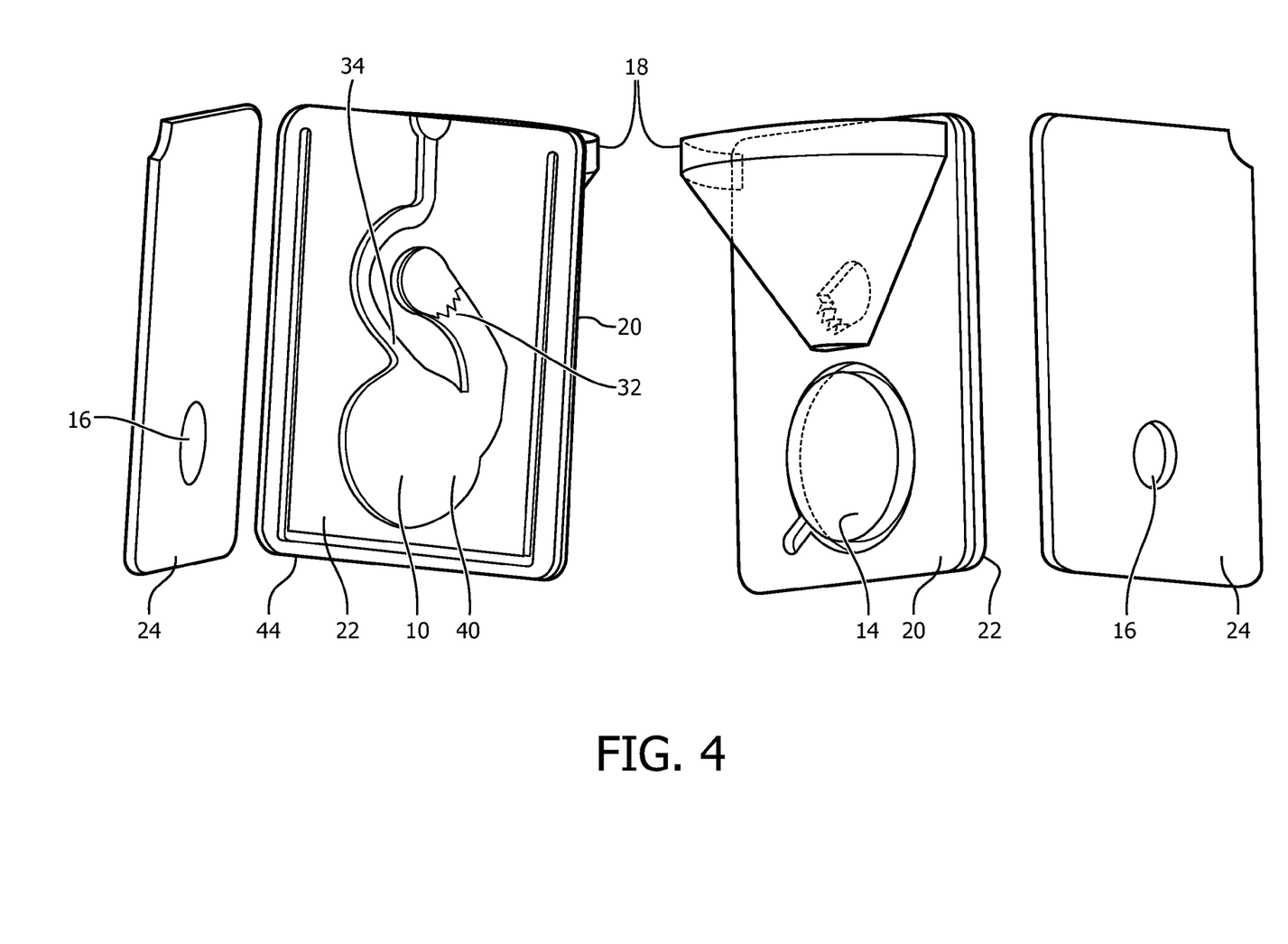
Figure 5:
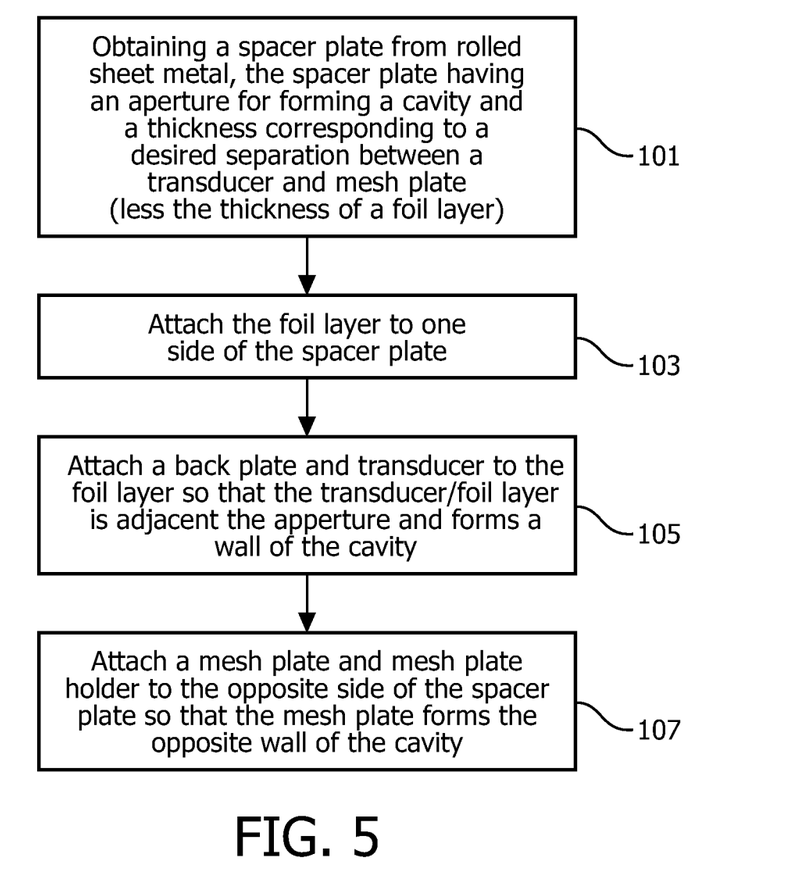

FIG. 3 is an exploded view of a nebulizer 2 according to a preferred embodiment of the invention, showing the components required to construct a nebulizer 2 so that the required tolerance on transducer 14 and mesh plate 16 separation is achieved.

As shown in FIG. 3, the nebulizer 2 comprises three plates 20, 22, 24 that are to be assembled in a stack to form the main part of the nebulizer 2. The first plate, 20, referred to herein as the back plate 20, has a hole 26 for receiving the transducer 14.

The second plate 22, referred to herein as the spacer plate 22, comprises an aperture 28 that forms the cavity 10 when the nebulizer 2 is assembled. The aperture 28 is positioned in the spacer plate 22 so that it is adjacent to the transducer 14 when the spacer plate 22, back plate 20 and third plate 24 are assembled to form a nebulizer 2.

The aperture 28 in the spacer plate 22 in the illustrated embodiment is generally circular as it is to approximately match the size of the transducer 14 (which in this embodiment is also circular) so that the volume of liquid in the cavity 10 exposed to the vibration of the transducer 14 at any one time is maximized (thereby helping to increase the mass flow rate provided by the nebulizer 2).

The third plate 24, referred to herein as the mesh plate holder 24, comprises the mesh plate 16. The mesh plate 16 is positioned in the mesh plate holder 24 so that it is adjacent to the aperture 28 in the spacer plate 22 when the plates 20, 22, 24 are assembled into the nebulizer 2.

When the three plates are assembled, the mesh plate 16, mesh plate holder 24, aperture 28 and transducer 14 form the cavity 10 for holding the liquid 12 to be nebulized. The side of the transducer 14 facing the spacer plate 22 is typically aligned with the side of the back plate 20 facing the spacer plate 22, and the side of the mesh plate 16 facing the spacer plate 22 is likewise aligned with the side of the mesh plate holder 24 facing the spacer plate 22. Thus, the thickness of the spacer plate 22 generally determines the separation between the transducer 14 and mesh plate 16. In the example provided in FIG. 1, a spacer plate 22 having a thickness of around 700 microns (0.7 mm) would be required in order for the nebulizer 2 to achieve the maximum possible flow rate.

Preferably, at least the spacer plate 22 is formed from metal, since it is relatively easy to manufacture components from metal to the tolerances required in nebulizers 2 (e.g. a thickness to within 10 microns) using known processes. Even more preferably, at least the spacer plate 22 is formed from rolled sheet metal. The aperture 28 and any other feature of the plate 22 can be formed using laser cutting techniques, although those skilled in the art will be aware of other techniques that can be used. A suitable metal for use in forming at least the spacer plate 22 according to the invention is stainless steel since it is a relatively low-cost material, it is easy to work into a plate with the required thickness and cut-outs, it is wear resistant and should maintain the required dimensions despite the nebulizer 2 being frequently dismantled for cleaning and then reassembled, and it is not likely to be corroded or worn through contact with the liquids 12 typically used in nebulizers 2. Stainless steel is also thermally stable so regularly heating the spacer plate 22 up to 95° C. during cleaning will not alter the dimensions and performance of the nebulizer 2. Alternatively, at least the spacer plate 22 can be formed from titanium or a titanium alloy (although these materials are not as low cost as stainless steel), or glass or a ceramic material (although these are more fragile than metal).

The spacer plate 22 and back plate 20 are typically rigidly attached to each other (for example using glue or another type of adhesive, bonding or fixing mechanism), so the spacer plate 22 and back plate 20 are preferably formed from the same material, such as metal (e.g. stainless steel). Although the mesh plate 16 and mesh plate holder 24 are designed to be disposable items, and therefore it may be desirable to form the mesh plate holder 24 from a cheaper material such as plastic, the mesh plate holder 24 is preferably also formed from metal, such as stainless steel, in order to ensure that the required tolerances on transducer and mesh plate spacing are met.

Although not shown explicitly in FIG. 3, the mesh plate holder 24 is configured so that it can be detached and removed from the rest of the nebulizer 2 (i.e. spacer plate 22 and back plate 20) so that the mesh plate 16 can be cleaned or the entire mesh plate holder 24 replaced. To this end, the spacer plate 22 or other component of the nebulizer 2 is provided with a clamping or other attachment mechanism for holding the mesh plate holder 24 in place adjacent to the spacer plate 22.

The back plate 20 can also include some clamping or other attachment mechanism for retaining the transducer 14 in place in the nebulizer 2. Alternatively, the transducer 14 can be glued or otherwise rigidly fixed to the back plate 20 or spacer plate 22.

Where one of more of the components of the nebulizer 2 are adhered or bonded together (such as the back plate 20/transducer 14 to the spacer plate 22), the thickness of the bonding layer should be taken into account when setting the distance between the transducer 14 and mesh plate 16. That is, the distance between the transducer 14 and mesh plate 16 will be equal to the thickness of the spacer plate 22 plus the thickness of any bonding layer(s), and the spacer plate 22 should be manufactured accordingly. In preferred embodiments, the thickness of the adhesive or bonding layer is controlled by adding spacer particles having known (and highly precise) dimensions to the adhesive or bonding material used to join the components together so that the spacer particles define the spacing between the components.

Although in the illustrated embodiment the mesh plate 16 has a smaller cross-sectional area than the aperture 28 and transducer 14, it will be appreciated that in other embodiments the cross-sectional area of the mesh plate 16 can be generally the same as the aperture 28 and transducer 14.

Furthermore, although FIG. 3 shows the mesh plate 16 as being separable from the mesh plate holder 24, it will be appreciated that the mesh plate 16 is typically integrated into the mesh plate holder 24.

In the illustrated embodiment, a reservoir chamber 18 is attached to the back plate 20 (opposite the side of the back plate 20 that faces the spacer plate 22) to hold further liquid 12 that is to be nebulized during operation of the nebulizer 2. A second hole 30 is formed in the back plate 20 to allow liquid 12 to pass through the back plate 20 and into the cavity 10.

Preferably, the second hole 30 does not have a fully rounded lower edge (since a fully rounded edge could form a barrier to liquid flow due to the surface tension of the liquid 12), and therefore at least a part of the lower edge of the second hole 30 has a jagged or saw-tooth profile in order to 'puncture' the surface of the liquid 12 and improve the flow of liquid 12 through the second hole 30.

As shown, the aperture 28 in the spacer plate 22 that forms the cavity 10 comprises a feed channel 32 to connect the cavity 10 between the transducer 14 and mesh plate 16 to the reservoir chamber 18. It will be appreciated that although the feed channel 32 is shown in FIG. 3 as having been cut through the spacer plate 22, it is possible for the feed channel 32 to be a groove or other indentation in the side of the spacer plate 22 facing the back plate 20.

It may be necessary to provide a vent through which air can escape when the cavity 10 is filled with liquid 12 from the reservoir chamber 18, so the spacer plate 22 further comprises a relatively narrow venting channel 34 that extends from the aperture 28 to an edge (preferably a top edge) of the spacer plate 22. As with the feed channel 32, although the venting channel 34 is shown in FIG. 3 as having been cut through the spacer plate 22, it is possible for the venting channel 34 to be a groove or other indentation in a side of the spacer plate 22.

To prevent any leakage of liquid 12 from the cavity 10 and feed channel 32 when the nebulizer 2 is in use, a sealing component 36, such as a rubber seal, can be provided between the spacer plate 22 and mesh plate holder 24. Preferably, to ensure that the sealing component 36 is held in the correct position when the mesh plate holder 24 is assembled into the nebulizer 2, a sealing component channel 38 is formed in the side of the mesh plate holder 24 that faces the spacer plate 22 that receives the sealing component 36.

Although not required in the embodiment shown in FIG. 3, in some embodiments a corresponding sealing component 36 can be provided between the spacer plate 22 and the back plate 20. In this case, a corresponding sealing component channel 38 can be formed in the spacer plate 22 or back plate 20.

In some embodiments of the invention, the spacer plate 22 can be attached directly to the back plate 20, in which case the transducer 14 can be covered with a metal, plastic or polymer protection layer to avoid direct contact between the transducer 14 and the liquid 12 in the cavity 10.

However, in preferred embodiments, a foil layer 40 is provided between the spacer plate 22 and the back plate 20 that acts to separate the transducer 14 from the liquid 12 in the cavity 10. In this preferred embodiment, the combined thickness of the foil layer 40 and spacer plate 22 (and any adhesive layers, if present) determines the separation between the transducer 14 and the mesh plate 16. The foil layer 40 can have similar dimensions (i.e. height and width) to the plates 20, 22, 24 as shown in FIG. 3, but it will be appreciated that the foil layer 40 is considerably thinner than the plates 20, 22, 24.

The foil layer 40 is preferably a metal foil since metallic foils absorb very little of the mechanical energy provided by the transducer 14 compared to plastic or polymer-based layers. The metal foil could be any hard biocompatible metal alloy, such as stainless steel. The foil layer 40 can have a thickness of the range of 1-200 microns, for example 50 microns. The foil layer 40 can be permanently attached to the back plate 20 and/or spacer plate 22, for example using a glue, adhesive or other bonding layer as described above (including spacer particles where appropriate).

The thickness of the adhesive or bonding layer between the transducer 14 and the foil layer 40 (or between the transducer 14 and the spacer plate 22 in those embodiments where a foil layer 40 is not present) can be around 50 micron. The thickness of the adhesive or bonding layer between the foil layer 40 and the spacer plate 22 can be around 10 micron. The thicker (or thick) layer of adhesive or bonding material between the transducer 14 and the foil layer 40 (or spacer plate 22 in those embodiments where a foil layer 40 is not present) is desirable for a number of reasons. Firstly, some transducers 14 comprise a disc of sintered ceramics, and the surface roughness is on the order of 10s of microns. Direct contact between the transducer 14 and metal (including the foil layer 40) should preferably be avoided, and therefore the adhesive or bonding layer can isolate the metal foil from the electric charge on the electrode of the transducer 14. In addition, the adhesive layer acts as a mechanical buffer, which is provided to absorb any strain in the lateral direction due to the different expansion coefficients of the transducer 14 and metal making up the foil layer 40 (although in the described embodiments these coefficients are quite similar). By absorbing the strain, the peak stress is lowered such that the transducer 14 does not detach from the foil layer 40 under its own action (vibration) or during the high temperatures to which the nebulizer 2 is exposed during cleaning.

Where a reservoir chamber 18 is provided on the back plate 20, a hole 42 is provided in the foil layer 40 that corresponds to the second hole 30 in the back plate 20 to allow liquid 12 to flow from the reservoir chamber 18 into the cavity 10. Where the second hole 30 has a jagged or saw-tooth lower edge, the hole 42 in the foil layer 40 will have a corresponding jagged or saw-tooth edge.

FIG. 4 shows two perspective views of a partially assembled nebulizer 2 according to an alternative embodiment of the invention. In FIG. 4, the back plate 20, transducer 14, reservoir chamber 18, foil layer 40 and spacer plate 22 have been assembled into a unit, and this unit forms the main part of the nebulizer 2. The mesh plate 16 and mesh plate holder 24 are detached from the main part of the nebulizer 2. The components in the alternative embodiment of FIG. 4 generally correspond to the embodiment shown in FIG. 3, except that an alternative arrangement for sealing the mesh plate holder 24 to the spacer plate 22 is shown. In this arrangement, a sealing component 44 is provided that extends around the periphery of the spacer plate 22.

An exemplary method of manufacturing part of a nebulizer 2 according to the invention is shown in FIG. 5. In step 101, a spacer plate 22 is obtained (e.g. fabricated) from rolled sheet metal having a thickness equal to the difference between the desired separation between a transducer 14 and a mesh plate 16 and the thickness of a foil layer 40 to be used in the nebulizer 2 (if present), along with the thickness of any adhesive or bonding layers used to assemble the components of the nebulizer 2 together. That is, the combined thickness of the spacer plate 22 and foil layer 40 (and adhesive layer(s)) is equal to the desired separation between a transducer 14 and a mesh plate 16. An aperture 28 is formed in the spacer plate 22 with dimensions that are similar to those of the transducer 14 to be used in the nebulizer 2. The aperture 28 is to define a cavity 10 in the nebulizer 2 for holding liquid 12 to be nebulized. The aperture 28 can be formed using laser cutting techniques.

In step 103, the metallic foil layer 40 is attached to one side of the spacer plate 22. The foil layer 40 can be attached to the spacer plate 22 using glue or another type of adhesive, and can include high-precision spacer particles that act to define the thickness of the adhesive layer as described above.

In step 105, a back plate 20 and transducer 14 are attached to the foil layer 40 so that the transducer 14 is adjacent the aperture 28 in the spacer plate 22 and the foil layer 40 and transducer 14 form one wall of the cavity 10. Again, glue or another type of adhesive with high-precision spacer particles can be used to attach the back plate 20 to the foil layer 40.

In step 107, which can occur during manufacture of the nebulizer 2 and/or prior to use of the nebulizer 2 by a patient, a mesh plate 16 in a mesh plate holder 24 is attached to the opposite side of the spacer plate 22 to the foil layer 40 and back plate 20 so that the mesh plate 16 forms the other wall of the cavity 10. As described above, the mesh plate holder 24 is typically attached to the spacer plate 22 in such a way as to allow removal and replacement of the mesh plate holder 24. Thus, the mesh plate holder 24 can be attached to the spacer plate 22 using a clamping mechanism.

Although FIG. 5 illustrates some exemplary steps for manufacturing part of the nebulizer 2 according to the invention, those skilled in the art will appreciate that a nebulizer 2 according to the invention can be manufactured using different steps, or a different order or combination of steps, to those illustrated. For example, step 103 could comprise attaching the foil layer 40 to the back plate 20 rather than to the spacer plate 22 with step 105 being adapted accordingly. Alternatively or in addition, steps 103, 105 and 107 could be performed in a different order to that shown. Further steps in the method can comprise steps of fabricating any one or more of the foil layer, back plate, mesh plate or mesh plate holder, including the fabrication of any channels or grooves in the plates for receiving a sealing component or for forming a venting or feed channel.

Although the invention has been described in terms of a nebulizer that is primarily for use in administering a medicament, it will be appreciated that the invention can be applied to any other type of nebulizer or device in which a transducer is actuated in order to nebulize a liquid through a mesh plate, such as, for example an air humidifier, an electric shaver, a steam iron or a perfume dispenser.

There is therefore provided a nebulizer that can be manufactured to the required tolerances and is low cost.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A nebulizer, comprising:

a first plate configured to hold a transducer;

a second plate having an aperture therein, the first plate being positioned on a first side of the second plate such that the transducer is adjacent the aperture;

a third plate configured to hold a mesh plate through which liquid can pass to form droplets, the third plate being positioned on a second side of the second plate opposite the first side such that the mesh plate is adjacent the aperture, with the aperture, transducer and mesh plate forming a cavity for holding liquid to be nebulized; and a reservoir chamber for holding further liquid to be nebulized, the reservoir chamber being linked to the cavity via a feed channel in the second plate that is in fluid communication with the first aperture in the second plate and a hole in the first plate.

2. A nebulizer as claimed in claim 1, wherein at least a part of a lower edge of the hole in the first plate has a jagged or saw-tooth profile.

3. A nebulizer as claimed in claim 1, the second plate further comprising a venting channel for venting the cavity.

4. A nebulizer as claimed in claim 1, wherein the first plate and second plate are fixedly attached together.

5. A nebulizer as claimed in claim 4, wherein the first plate and second plate are fixedly attached together using at least one adhesive or bonding layer, the adhesive or bonding layer comprising spacer particles therein for setting the thickness of the adhesive or bonding layer to a predetermined amount.

6. A nebulizer as claimed in claim 1, wherein the thickness of the second plate generally defines the separation between the transducer and the mesh plate.

7. A nebulizer as claimed in claim 1, the nebulizer further comprising a foil layer disposed between the first plate and the second plate to prevent contact between the transducer and liquid to be held in the cavity.

8. A nebulizer as claimed in claim 7, wherein the foil layer is a metal foil.

9. A nebulizer as claimed in claim 7, wherein the thickness of the foil layer and the thickness of the second plate generally defines the separation between the transducer and the mesh plate.

10. A nebulizer as claimed in claim 1, wherein at least the second plate is metal.

11. A nebulizer as claimed in claim 10, wherein at least the second plate is formed from rolled sheet metal.

12. A nebulizer as claimed in claim 10, wherein at least the second plate is rolled sheet stainless steel.

13. A nebulizer as claimed in claim 1, wherein the third plate and mesh plate are removably attached to the second plate.

14. A method of manufacturing a nebulizer, the method comprising:
  obtaining a second plate having an aperture therein;
  attaching a first plate that is configured to hold a transducer to a first side of the second plate such that the transducer is adjacent the aperture;
  attaching a third plate that is configured to hold a mesh plate through which liquid can pass to form droplets to a second side of the second plate opposite the first side such that the mesh plate is adjacent the aperture, with the aperture, transducer and mesh plate forming a cavity for holding liquid to be nebulized; and
  attaching a reservoir chamber for holding further liquid to be nebulized, the reservoir chamber being linked to the cavity via a feed channel in the second plate that is in fluid communication with the first aperture in the second plate and a hole in the first plate.

* * * * *